US009826947B2

(12) United States Patent
Young

(10) Patent No.: US 9,826,947 B2
(45) Date of Patent: Nov. 28, 2017

(54) FLEXIBLE ANTISCATTER GRID

(71) Applicant: Carestream Health, Inc., Rochester, NY (US)

(72) Inventor: Ted G. Young, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 220 days.

(21) Appl. No.: 14/629,512

(22) Filed: Feb. 24, 2015

(65) Prior Publication Data

US 2016/0247590 A1 Aug. 25, 2016

(51) Int. Cl.
*A61B 6/00* (2006.01)
*G21K 1/02* (2006.01)
*G21K 1/10* (2006.01)

(52) U.S. Cl.
CPC ............ *A61B 6/4291* (2013.01); *G21K 1/02* (2013.01); *G21K 1/025* (2013.01); *G21K 1/10* (2013.01)

(58) Field of Classification Search
CPC .......... A61B 6/4291; G21K 1/02; G21K 1/10
USPC ............... 378/19, 98.8, 147, 149, 154, 155; 250/370.09
See application file for complete search history.

(56) References Cited

U.S. PATENT DOCUMENTS

| | | | |
|---|---|---|---|
| 2,605,427 A | 7/1952 | Delhumeau | |
| 4,951,305 A | 8/1990 | Moore et al. | |
| 5,557,650 A | 9/1996 | Guida et al. | |
| 5,581,592 A | 12/1996 | Zarnoch et al. | |
| 5,606,589 A * | 2/1997 | Pellegrino | A61B 6/502 378/147 |
| 6,064,720 A * | 5/2000 | Piscitelli | A61B 6/00 378/154 |
| 6,185,278 B1 * | 2/2001 | Appleby | G21K 1/025 378/149 |
| 6,408,054 B1 | 6/2002 | Rahn et al. | |
| 6,895,080 B2 * | 5/2005 | Baba | G21K 1/025 378/147 |
| 7,141,812 B2 * | 11/2006 | Appleby | B29C 33/302 250/505.1 |
| 7,410,606 B2 * | 8/2008 | Appleby | B23P 15/246 249/117 |
| 7,462,852 B2 * | 12/2008 | Appleby | B29C 33/3842 250/505.1 |
| 7,518,136 B2 * | 4/2009 | Appleby | B29C 33/3842 250/505.1 |
| 7,785,098 B1 * | 8/2010 | Appleby | B29C 33/302 264/319 |
| 7,787,596 B2 * | 8/2010 | Hempel | G01N 23/046 378/145 |
| 7,801,279 B2 * | 9/2010 | Jans | G21K 1/025 378/154 |
| 7,839,981 B2 * | 11/2010 | Kammel | G21K 1/025 378/149 |
| 8,217,359 B1 * | 7/2012 | Kross | G21K 1/02 250/370.09 |

(Continued)

*Primary Examiner* — Allen C. Ho

(57) ABSTRACT

An antiscatter grid for radiological imaging, the grid formed as a stack of two or more sheets having a flexible substrate, wherein each sheet has spaced-apart opaque cavities, each opaque cavity containing a radio-opaque material. The opaque cavities define a plurality of channels that extend through the sheets to allow ionizing radiation to pass therethrough. Magnets disposed along the sheets couple each sheet to one or more neighboring sheets of the stack.

20 Claims, 17 Drawing Sheets

(56) References Cited

U.S. PATENT DOCUMENTS

| | | | |
|---|---|---|---|
| 8,821,015 B2* | 9/2014 | Stagnitto | A61B 6/4291 |
| | | | 378/205 |
| 8,971,498 B2* | 3/2015 | Haider | G21K 1/10 |
| | | | 378/147 |
| 9,047,999 B2* | 6/2015 | Beck | G21K 1/025 |
| 9,048,002 B2* | 6/2015 | Beck | G21K 1/025 |
| 9,315,663 B2* | 4/2016 | Appleby | C08L 63/00 |

* cited by examiner

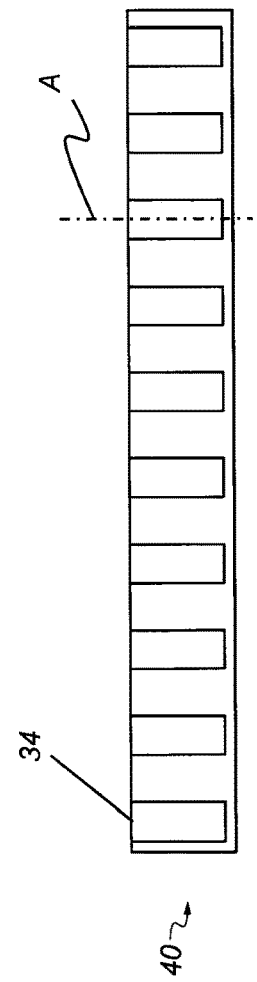

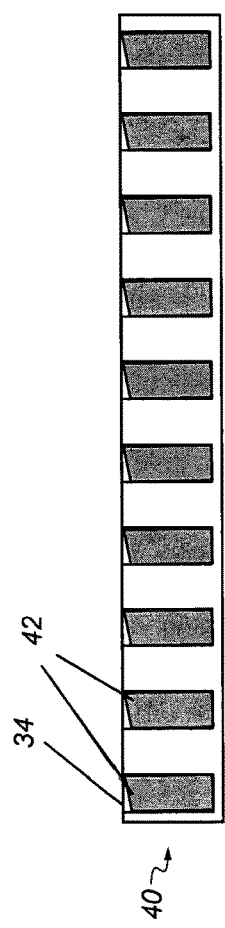
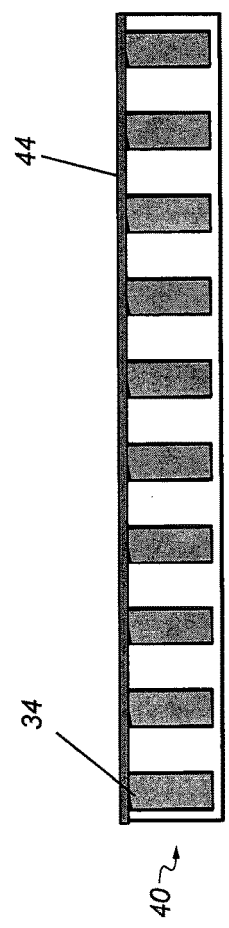
FIG. 7C
FIG. 7D

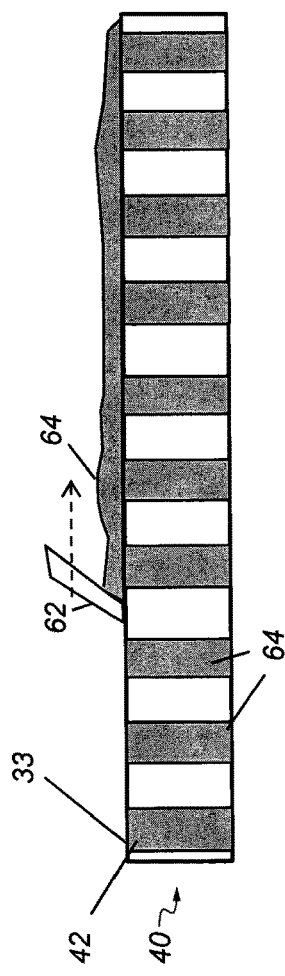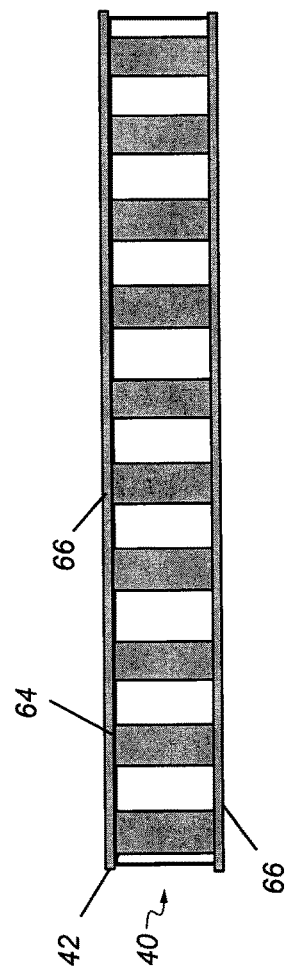

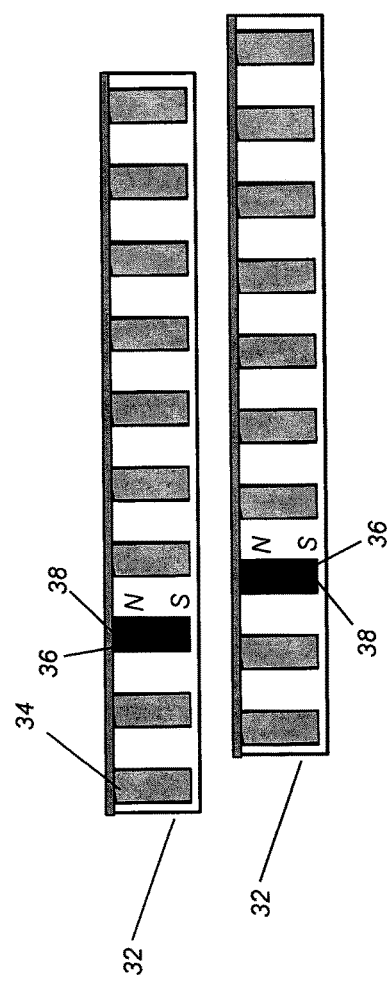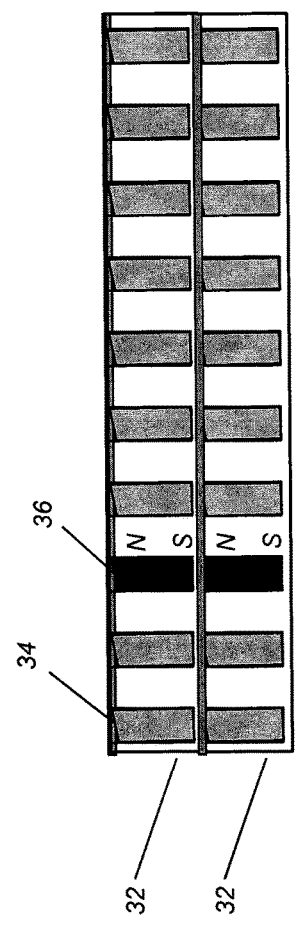

FLEXIBLE ANTISCATTER GRID

FIELD OF THE INVENTION

The invention relates generally to the field of diagnostic imaging and more particularly to apparatus and methods for providing a flexible antiscatter grid to reduce scatter effects in a radiographic image.

BACKGROUND OF THE INVENTION

Scattered radiation presents a particular challenge for radiographic imaging. In some cases, scatter can significantly reduce subject contrast, making it difficult to discern various anatomical features in the radiographic image.

Linear grids have been devised in order to help correct this problem. Linear grids are antiscatter devices that are used to improve contrast and to improve the signal to noise ratio in radiographic images. A conventional antiscatter grid typically consists of a series of lead foil strips separated by spacers that are transmissive to x-rays. The spacing of the strips determines the grid frequency, and the height-to-interspacing distance between lead strips determines the grid aspect ratio. Grids can be oriented horizontally or vertically relative to the imaging medium.

There are two general types of antiscatter grids: moving (Bucky-Potter configuration) and stationary. For moving type grids, the shadows of the lead strips are blurred out by motion, which can be either reciprocating or unidirectional (single stroke). For stationary grids, the shadows of the lead strips are imposed onto the radiographic image and can be reduced using programmed image processing methods.

In general, antiscatter grids, equivalently termed "image contrast antiscatter grids", are required for most types of "thick" tissue medical imaging procedures; i.e., procedures in which the screen is not located close (within about the thickness of the screen) to body tissue during medical imaging procedures.

Image contrast antiscatter grids have been formed in a number of ways. Grids can be formed by laminating together foils of x-ray transparent material, such as aluminum and x-ray absorbing material, such as lead, to form an extended sandwich structure. The simplified schematic of FIG. 1 illustrates a known sandwich structure image contrast antiscatter grid 24 including aluminum foils 26 and lead foils 28 forming an alternating, parallel arrangement.

Other methods of forming image contrast antiscatter grids have been described, for example, in U.S. Pat. Nos. 5,581,592 and 5,557,650, which are incorporated herein by reference in their entirety.

The various methods proposed for forming antiscatter grids have proved to be cumbersome or unsatisfactory for a number of reasons, including:

(i) high cost, due in large part to complex and expensive fabrication;
(ii) significant weight, making the grid difficult to position;
(iii) grid visibility in the acquired image; [Known image contrast antiscatter grids, such as the image contrast antiscatter grid 24 in FIG. 1, have a relatively coarse structure that produces grid lines in radiographic images. To reduce this problem, for example, the grids can be moved slightly back and forth in a direction approximately perpendicular to the normal (that is, slightly back and forth perpendicular to the direction of the x-rays) to blur the image of the grid lines formed on the receiver. This movement of the grids is known as the "Bucky system." However, the Bucky system requires the imaging system to include additional components and, thus, increases the cost and complexity of the system.]
(iv) incomplete scatter compensation; [Known image contrast antiscatter grids, such as the image contrast antiscatter grid 24 of FIGS. 1 and 2, only remove the Compton-scattered, non-normal (off-z-axis) photons in one dimension (i.e., along either the x-axis or the y-axis). In order to provide two-dimensional photon removal using these grids, two grids, such as two of the image contrast antiscatter grids 24, must be stacked with their respective foils oriented orthogonally with respect to each other. Although the combined use of two grids may improve Compton-scattered photon removal in a second direction, the cost of the imaging system is significantly increased by the added cost of the second grid. Thus, the value of improving the performance of the imaging system by using two image contrast antiscatter grids may not justify the associated added cost and space requirements to achieve the improved performance.]
(v) fragile structure, readily damaged by mishandling;
(vi) rigidity, making the grid unusable in some applications; [Flexibility of the grid can have value in particular imaging applications, but is not currently available.] and
(vii) not readily adaptable to different imaging conditions.

In addition, grid use increases the required patient exposure, because of the needed compensation for absorption of primary radiation by the interspace material that forms the grid.

A greatly enlarged cross sectional portion of a simple, conventional image contrast anti-scatter grid 24 is schematically shown in FIG. 2. In the grid, slats of x-ray opaque lead foil 28 alternate with filler strips of x-ray transmissive aluminum foil 26 or fiber. The height of the grid is h, and the interspace width is w. The ratio r=h/w is known as the grid ratio. In practice, for this ratio, h/w=16/1 may be considered a maximum. To achieve this ratio without reducing a transmission magnitude of the grid requires a large number of slats (i.e., a small value of w), since the available h is limited by the current use and design of x-ray equipment to values of about two millimeters. Slats, generally formed of lead, add significantly to grid weight.

Another type of grid, shown in U.S. Pat. No. 2,605,427 issued Jul. 29, 1952, to Delhumeau is a two-dimensional focusing grid, so called because the slats are aligned with the rays coming from the x-ray source. Two-dimensional antiscatter grids can be nearly twice as heavy as one-dimensional grids due to the additional amounts of x-ray absorbent material that are needed.

U.S. Pat. No. 6,408,054 to Rahn et al. describes a micromachined contrast grid having numerous tiny holes formed by etching and photolithography, for example. The holes can be of selected depths and angles. The holes are then filled with small amounts of lead or other x-ray absorbing material to form a grid pattern. Various coating processes are described for filling the cylindrical holes formed in the grid substrate.

Among solutions proposed for grid fabrication is forming multiple sheets and aligning the sheets to each other to define the path of incident radiation through the grid. U.S. Pat. No. 4,951,305 to Moore et al. describes one approach to this problem using aligned sheets. Accurate alignment of multiple sheets to each other, however, proves to be difficult, even where extremely tight manufacturing tolerances are maintained. Moreover, subsequent handling of the grid can easily cause inadvertent misalignment of the successive sheets used in such an arrangement.

Rigid grids do not adapt to nonplanar detector surfaces and allow only a very small focus range. Because grids have traditionally been formed using lead strips separated by aluminum spacing material, grids have been formed as rigid, planar devices that do not flex. However, there may be some applications for which some amount of grid flexure is of value. Existing approaches used for grid fabrication do not allow flexibility of the grid.

It can thus be appreciated that there are advantages to grid design that helps to remedy one or more of the identified factors that make conventional grids cumbersome or unsatisfactory for use.

SUMMARY OF THE INVENTION

An object of the present disclosure is to advance the art of radiography and to address the need for fabrication of a flexible grid. Features of the present disclosure include improved capabilities for alignment of sheets in a multiple-sheet grid.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the disclosure, there is provided an antiscatter grid for radiological imaging, the grid formed as a stack of two or more sheets of a flexible substrate, wherein each sheet has:
 (i) a plurality of spaced-apart opaque cavities, each opaque cavity containing a radio-opaque material and wherein the arrangement of opaque cavities within the stack of sheets defines a plurality of channels for ionizing radiation that extend through the sheets; and
 (ii) a plurality of magnets that are disposed along the sheet and that couple the sheet to one or more neighboring sheets within the stack.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 7A is a side view that shows an exemplary starting substrate to be fabricated into a sheet of an antiscatter grid.

FIG. 7B is a side view that shows cavities formed in the exemplary starting substrate of FIG. 7A.

FIG. 7C shows filling the cavities in the exemplary substrate with radio-opaque material.

FIG. 7D shows covering the filled cavities to form an exemplary finished sheet.

FIGS. 8A and 8B show an alternate exemplary sequence for filling holes and for sealing an individual sheet.

FIG. 9A shows a side view of two exemplary grid sheets assembled to use magnet-assisted alignment.

FIG. 9B shows magnet-assisted alignment between portions of two exemplary sheets.

DETAILED DESCRIPTION OF THE INVENTION

Figure 1:
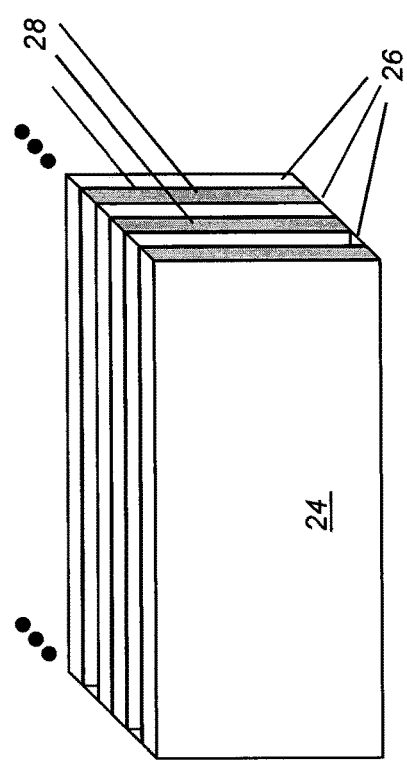
FIG. 1 is a schematic view in perspective showing parts of an exemplary conventional antiscatter grid.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "subject" refers to the patient who is being imaged and, in optical terms, can be considered equivalent to the "object" of the corresponding imaging system.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

In the context of the present disclosure, the term "oblique" means at an angle that is not an integer multiple of 90 degrees. Two lines, linear structures, or planes, for example, are considered to be oblique with respect to each other if they diverge from or converge toward each other at an angle that is at least about 10 degrees or more away from parallel, or at least about 10 degrees or more away from orthogonal.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

Radio-opaque materials are those that absorb and thus attenuate the x-ray beam significantly enough for detection and radiographic imaging and are considered to be non-transparent to x-rays at given energy levels. A well known radio-opaque material typically used for grids is lead. Radio-lucent or transmissive materials do not significantly absorb or attenuate the x-ray radiation.

Non-magnetic materials are materials that are negligibly affected by magnetic fields and that exhibit no perceptible magnetic attraction and are thus not perceptibly pulled toward a magnet. In general, non-magnetic materials have a low relative magnetic permeability, typically not exceeding 1.0 at room temperature. Some exemplary non-magnetic materials include copper, aluminum, standard stainless steel, and most metals and alloys; sapphire; various ceramics; wood and paper composite materials; glass; water; plastics and other polymers; fiberglass; and various composite materials such as phenolic materials. Magnetic materials have higher relative permeability and are considered to be "magnetically responsive", exhibiting magnetic attraction that can be readily perceived without requiring instrumentation; this includes ferromagnetic materials and various compounds of rare earth materials, for example.

There are two general classes of ferromagnetic materials. Permanent magnets are made from "hard" ferromagnetic materials such as alnico and ferrite that are subjected to special processing in a powerful magnetic field during manufacture, to align their internal microcrystalline structure to exhibit a magnetic flux field. Magnetically "soft" materials like annealed iron, on the other hand, can be magnetized for a period of time, but do not tend to stay magnetized. To demagnetize a saturated magnet, a magnetic field of a given threshold must be applied, and this threshold depends on coercivity of the respective material. "Hard" materials that behave as permanent magnets have high coercivity, whereas "soft" materials have low coercivity. By way of example, electrical steel, used as a flux carrier in many electrical devices, exhibits coercivity values in the range of about 0.5 oersteds; samarium cobalt, used for rare earth permanent magnets, has coercivity in the range of about 40,000 oersteds.

In the context of the present disclosure, a flexible sheet is a sheet that can be bent from a substantially flat planar form over a bend radius of 100 millimeters or less and can be restored to substantially flat planar form without damage.

Embodiments of the present invention address a number of problems that relate to grid fabrication and can be used to form an antiscatter grid that is flexible. The methods and apparatus of the present invention can be used to configure a wide range of grid patterns to allow for various radiographic imaging applications.

Figure 3:
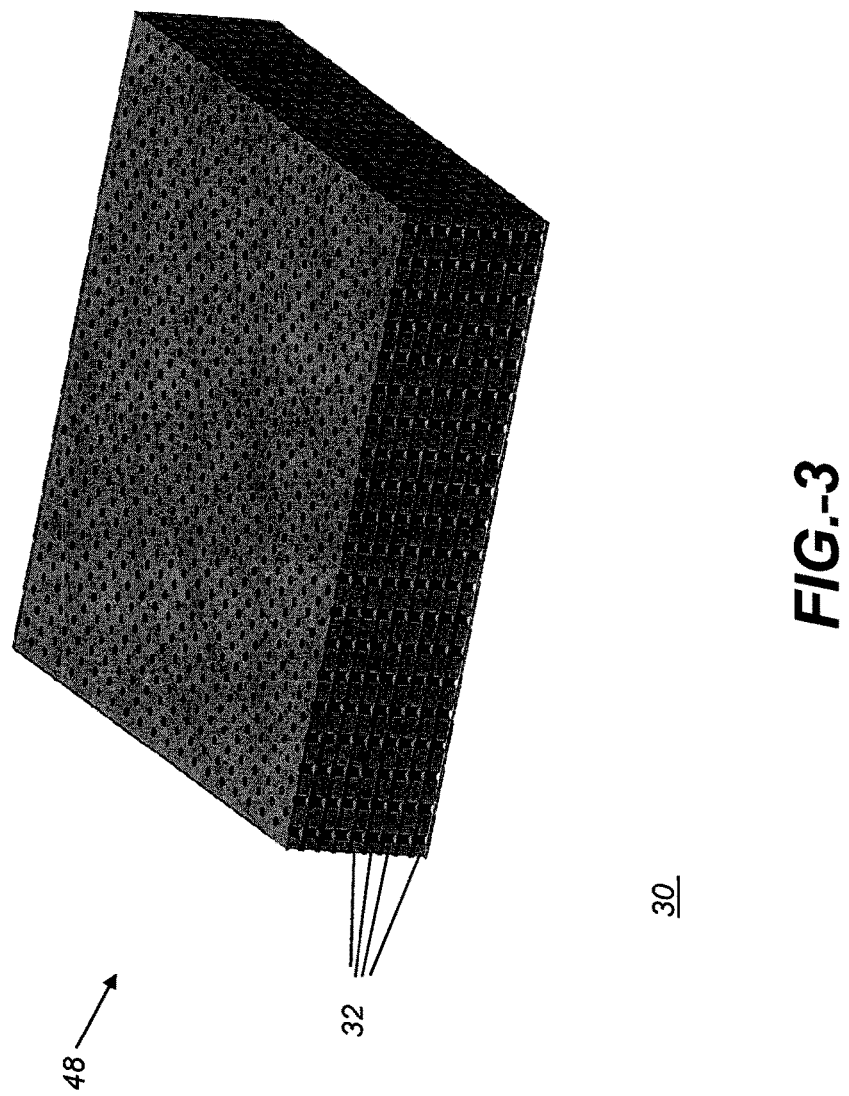
FIG. 3 is a perspective view showing an antiscatter grid according to an exemplary embodiment of the present disclosure.

The perspective view of FIG. 3 shows schematic representation of a grid 30 formed according to an embodiment of the present disclosure. Features are not shown to scale, but are exaggerated in size to represent their physical arrangement. Grid 30 is formed as a stack 48 of sheets 32 that are aligned in a suitable arrangement for a particular imaging application. There are nine sheets 32 according to an embodiment of the present disclosure shown in FIG. 3. The number of sheets 32 that are used can be varied, allowing grid 30 to be formed from a stack 48 of as few as two sheets 32, or more. Each sheet 32 is formed from a flexible material that has numerous radio-opaque cavities 34 that are filled with radio-opaque material 42. Successive sheets 32 in the stack 48 are registered to each other so that their respective radio-opaque cavities 34 align to provide a suitable pattern of clear channels bounded and defined by the radio-opaque cavities 34. Thus, each neighboring sheet 32 can be the same or can be separately configured.

Figure 4:
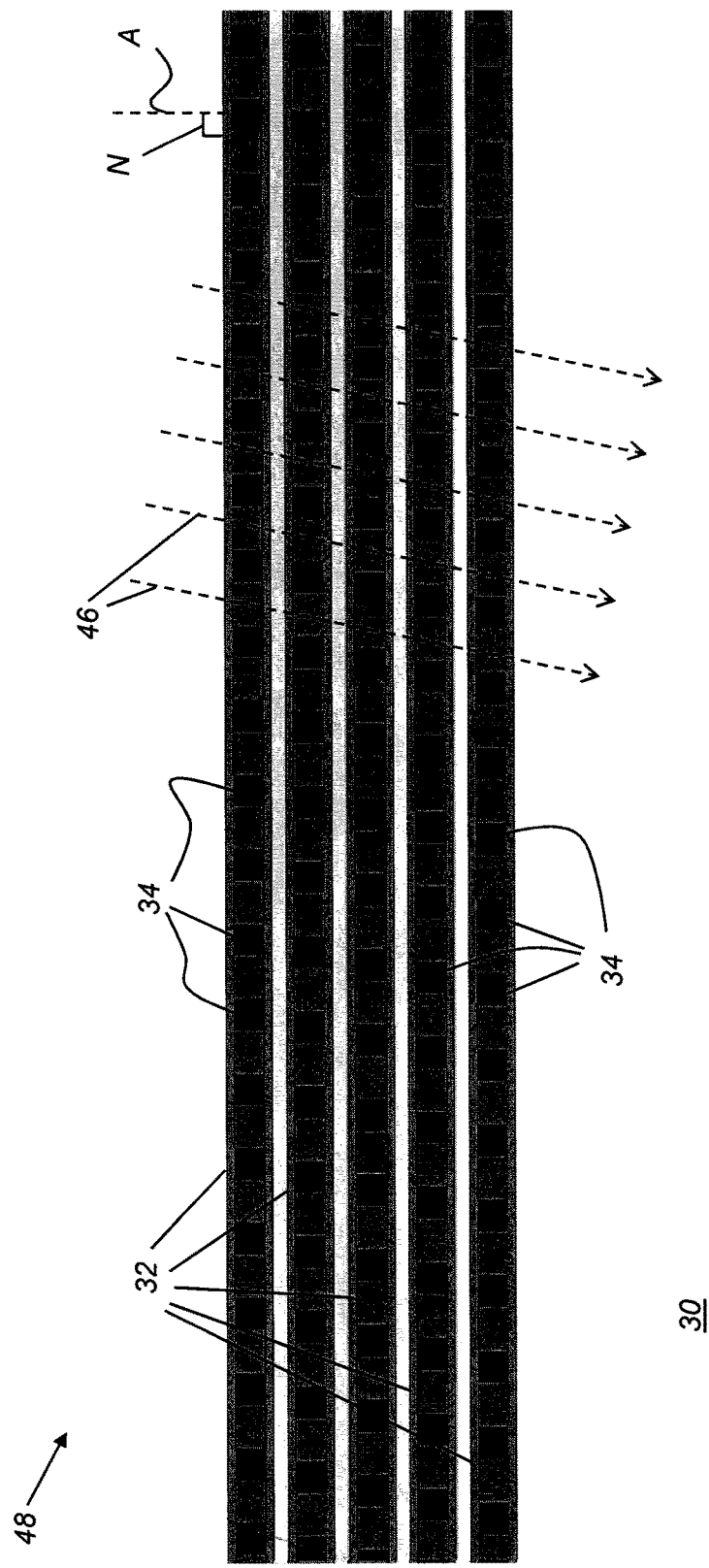
FIG. 4 is a side view that shows an exemplary staggered arrangement of sheets that form an antiscatter grid.

As shown in FIG. 4, alignment of radio-opaque cavities 34 defines how clear channels 46 are arranged in the stack 48. Groups of aligned radio-opaque cavities 34 in successive sheets 32 can each be formed along an axis, with the axes of the groups of radio-opaque cavities 34 converging toward a focal point that lies some distance outside the sheet 32. Sheets 32 stacked to form an antiscatter grid can have radio-opaque cavities 34 directed toward the focal point so that, when the full set of sheets 32 for an antiscatter grid are stacked, clear channels 46 are formed extending from the top of the stack 48 to the bottom, with the clear channels 46 inclined toward the focal point. Cavities 34 themselves can each be formed along an axis A that is normal (angle N) to the sheet surface, with focus provided by staggering respective axes A of each of the radio-opaque cavities 34 from one sheet 32 to the next, so that radio-opaque cavities 34 on each sheet 32 are offset slightly from those on the neighboring sheet 32, effectively forming a substantially clear channel 46 for radiation when the sheets 32 are stacked, as shown in FIG. 4.

Figure 2:
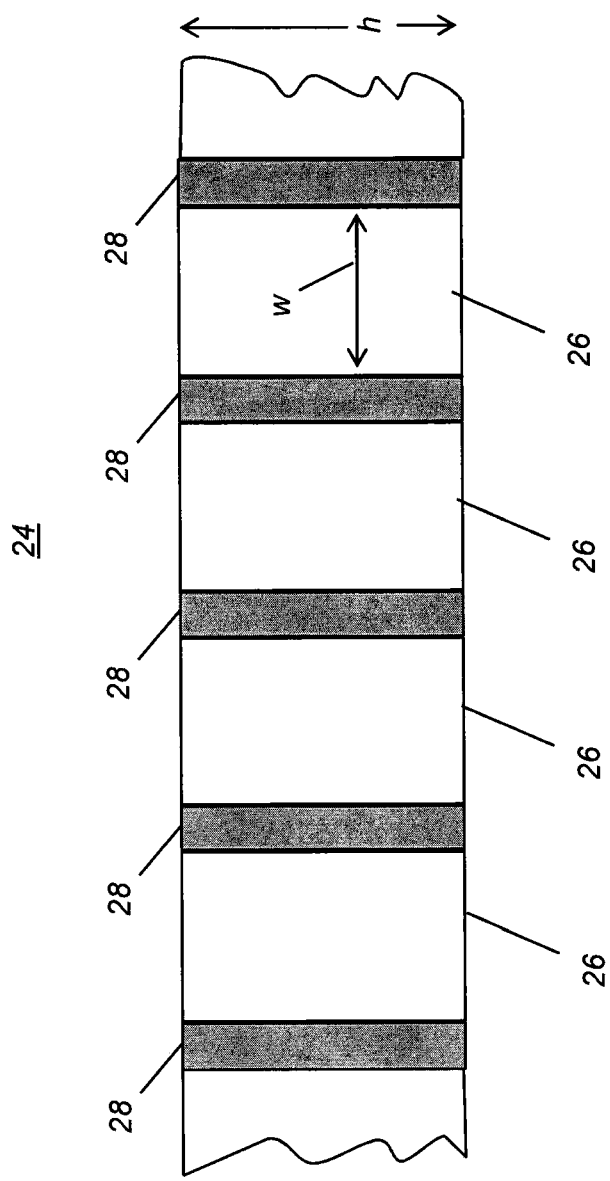
FIG. 2 is a cross-sectional side view of the exemplary conventional grid of FIG. 1, showing dimensional definitions.

Cavities 34 can be tiny and may not be visible to the unaided eye, so that each sheet 32 can have as many as a few million radio-opaque cavities 34, each extending within sheet 32 in the depth direction (h in FIG. 2) from one major surface (upper or lower) to the other major surface (lower or upper). The exploded side view of FIG. 4 shows a portion of one possible stack 48 arrangement, in which radio-opaque cavities 34 are formed along axes A normal to a surface of each sheet 32, which sheets 32 are successively staggered in the horizontal direction with respect to each neighbor sheet 32, for the orientation shown. This type of arrangement may provide oblique clear channels 46 formed by the stack 48 for focusing of incident radiation to form a focused grid 30, for example. Other arrangements can be envisioned for special purpose imaging, taking into account factors such as source-to-image distance (SID), grid resolution, amount of scatter compensation that is needed, and the like.

Sheet Substrate

Figure 5:
FIG. 5 is a side view that shows exemplary angled holes formed in a single sheet.

In order to provide a flexible grid 30, sheet 32 may be formed from a material that is substantially transparent to radiation and that is also flexible. Substrates 40 that can be used for forming sheet 32, such as shown in FIG. 5, include, but would not be limited to, various polymer materials including polyester and Polyethylene Terephthalate (PET), for example. The substrate sheet material can be dimensionally stable in the plane of the sheet 32 but flexible out of the plane.

Forming Sheet Cavities

Cavities 34 can be formed in any of a number of ways, depending on size and spacing requirements and properties of the substrate that is used. According to an embodiment of the present disclosure, radio-opaque cavities 34 and other features (e.g., holes) are formed by sheet treatment with a laser, such as a $CO_2$ laser, to form holes or cavities through a sheet 32 initially. Lasers from Universal Laser Systems, Trotec Laser Systems, or other manufacturers can be used. FIG. 5 shows a cross section of finished sheet 32 formed with angled radio-opaque cavities 34.

Figure 6:
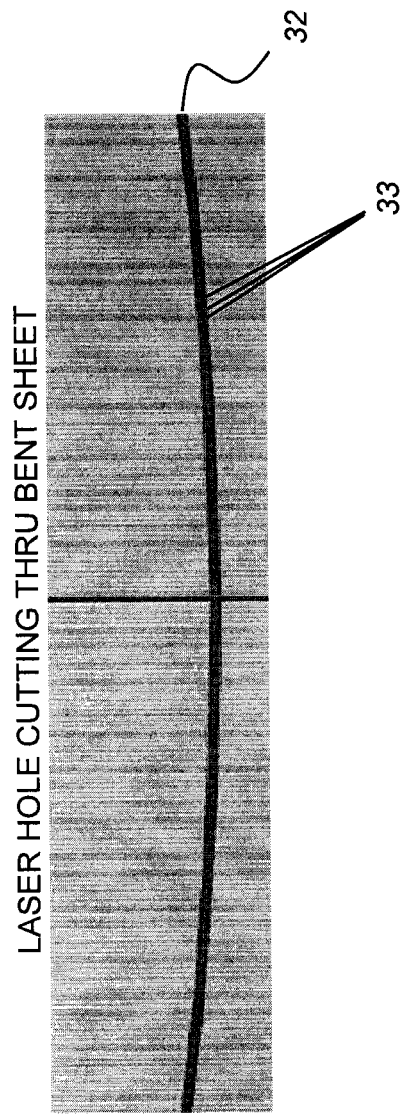
FIG. 6 is a side view that shows one exemplary method for cutting angled holes in a sheet.

The side view of FIG. 6 shows one method for forming holes 33 through one or more sheets 32. Using this technique, one or more sheets 32 are bent about a radius having a preselected magnitude; then, a laser is used to form holes 33 through the one or more sheets 32. When a sheet 32 that has been treated in this way is straightened, the resulting holes 33 may be disposed at variably controlled angles.

Holes 33 or radio-opaque cavities 34 in a plurality of stacked sheets 32 may also be drilled or otherwise formed simultaneously. Where this is done, the holes 33 may extend fully through several sheets 32. Other methods can be used for forming radio-opaque cavities 34, including molding, perforation, drilling, and etching, for example. Each radio-opaque cavity 34 or hole 33 may have a diameter of about $2/1000$ of an inch or less. Cavities 34 can be uniformly sized and spaced. Alternately, radio-opaque cavities 34 may have variable size and/or spacing along the sheet 32.

Filling Sheet Cavities

The fabrication sequence shown in FIGS. 7A through 7D shows how sheet 32 can be formed, according to an embodiment of the present disclosure. A flexible substrate 40 is shown in FIG. 7A. A cavity-forming operation is then used to form an array of tiny cavities 34, as shown in FIG. 7B. As noted previously, each cavity 34 can have a central axis A that may be normal to the flexible substrate 40 surface or may be oblique with respect to the flexible substrate 40 surface. Then, as shown in FIG. 7C, a filling operation is performed, filling each cavity 34 with a radio-opaque material 42. FIG. 7D shows addition of an x-ray transparent sealant layer 44, which may be a thin sheet of the same substrate material, for example, or some other suitable sealing material to form a finished sheet 32. The additional x-ray, transparent sealant layer 44 can also be applied to the opposite side of flexible substrate 40. Where holes are drilled completely through the starting substrate sheet, sealing material or treatment is applied to both surfaces of the sheet, thereby transforming the filled hole into a filled cavity.

The radio-opaque material 42 that is used for filling holes or cavities 34 may be any of a number of materials and can be provided in nanoparticulate or powdered form, or provided in solution, such as an emulsion or colloidal solution, for example. Finely ground metals such as tungsten (W) or lead (Pb) can be used. Tungsten particulate is an advantageous alternative to lead. One commercially available tungsten powder (Buffalo Tungsten, type SR) has apparent powder density 8.5-10 $g/cm^3$. By way of reference, solid lead has a density of 11.3 $g/cm^3$.

According to an alternate embodiment of the present disclosure, as shown in the partial fabrication sequence of FIGS. 8A and 8B, a squeegee 62 is used to press a tungsten-based paste 64 as radio-opaque material 42 into holes 33. The high density emulsion can then be at least partially dried. Excess tungsten-based paste 64 is then scraped from the top and bottom of the filled substrate and a protective film 66 applied to both top and bottom surfaces to form the finished sheet. Alternately, particulate or nanoparticulate material could be forced into the holes 33 as radio-opaque material 42. According to an alternate embodiment of the present invention, radio-opaque material 42 is a particulate and is combined with a curing material that binds the particulate to the side walls of holes 33 (or cavities 34) so that no sealant layer 44 (FIG. 7D) or protective film 66 is needed.

Once holes 33 have been filled and sealed, assembly of the sheet 32 with other sheets 32 to form the grid can be performed. Sealing can also be performed using heat to encapsulate material within the cavity 34 or hole 33, or by using an adhesive, a hardener, or other material or process to encapsulate the radio-opaque material 42 or to harden the material into place.

Sheet Coupling and Alignment

Grid 30 can be formed from a number of suitably prepared sheets 32. To provide close registration between neighboring sheets 32 and all of the sheets 32 for a particular grid 30, holes 33 for all of the sheets 32 used for a grid 30 can be cut through at the same time. Angled cavities 34 may be created in a sheet 32 by forming a flexible substrate 40 in radius, then cutting holes 33 through the flexible substrate 40, then re-flattening the flexible substrate 40. Specialized, focused grid patterns may be formed, such as patterns that are suitably randomized to reduce or eliminate fringe patterns in the image that is obtained using the grid 30.

The area of the pattern of cavities 34 on the sheet 32 can be a standard grid size, such as 435 mm×435 mm [17.1"× 17.1"], for example. The stack 48 of sheets 32 forming the grid 30 can be about 42 cm×34 cm or about 42 cm×42 cm.

Sheet alignment is a particular challenge with cavities 34 of the number and size needed. Sheets 32 can be coarsely aligned by permanently fastening together, either at one end or in the middle of the sheet 32 or at the perimeter.

According to an embodiment of the present disclosure, sheets 32 are coarsely aligned in some way, then precision aligned and held together or coupled using magnetic attraction. Referring to the partial cross-section view of FIG. 9A, a pattern of cavities 34 are filled with a magnetized material 38 that give the corresponding magnetic cavities, now numbered cavities 36 in FIG. 9A and following, a particular magnetic polarity arrangement. Mutual attraction between magnetic cavities 36 that have magnetized material 38 causes these magnetic cavities 36 to align with each other and couple the sheets 32 together as shown in FIG. 9B.

According to an embodiment of the present disclosure, magnetized material 38 is selectively deposited into a patterned distribution of magnetic cavities 36, so that the pattern of magnetic cavities 36 is the same for adjacent sheets 32. The pattern can be a matrix of magnetic cavities 36, such as having a magnetic cavity 36 at every increment of a given number of millimeters from a given origin, for example. The magnetized material 38 is then magnetized (typically, permanently magnetized) so that magnetic poles north (N) and south (S) are oriented to correctly attract each sheet 32 to its adjacent neighboring sheet 32 for a magnetic coupling. The magnetization step can be performed using a fixture that is designed with magnetizing elements in accordance with the given pattern. This magnetization processing can be performed prior to filling cavities 34 or holes 33 with high density materials to form clear channels 46 (FIG. 4).

According to an alternate embodiment of the present invention, the patterned distribution of magnetic cavities 36 includes a matrix having both magnets and magnetic materials 38, such as ferrous materials that are magnetically responsive but are not themselves magnetized.

Figure 10A:
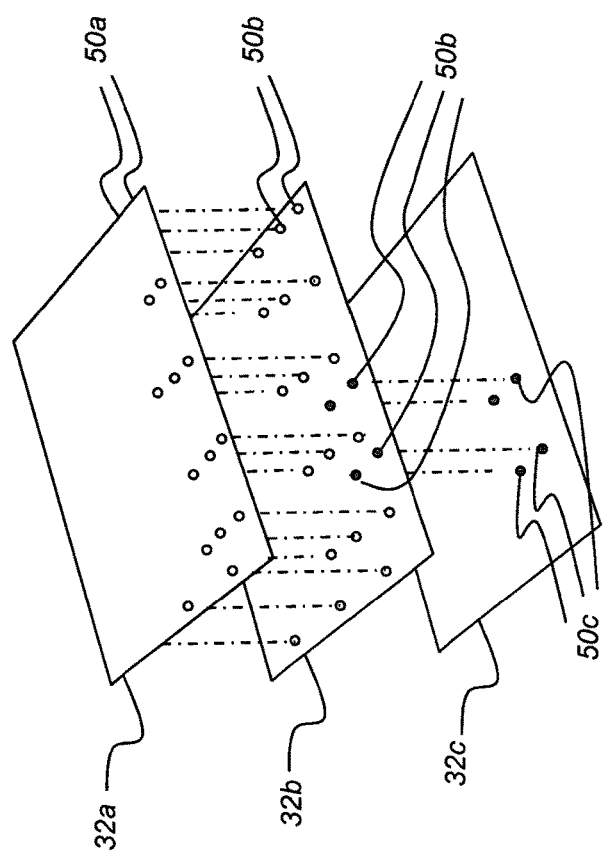
FIG. 10A is an exploded view that shows how magnetized material in the cavities may be used to magnetically align sheets that are placed in order.

The exploded view of FIG. 10A shows an alternate arrangement in which magnets 50a, 50b, 50c that are embedded within or coupled to the sheet can be used to magnetically couple and align neighboring sheets that may be placed in order, such as to provide radio-lucent channels 46 that are orthogonal to the sheet 32 surface or to provide oblique radio-lucent channels 46 using staggered-pattern sheets that allow the channeling of radiation in a focused manner. The same principles described with reference to magnets 50a, 50b, and 50c in FIG. 10A apply when using magnetized material 38 that is embedded within cavities 36, as described previously. In the example of FIG. 10A, three sheets are shown, labeled as sheets 32a, 32b, and 32c. Neighboring sheets 32a and 32b have corresponding magnets 50a and 50b, respectively, that are attracted to each other for coupling and alignment. Similarly, adjacent or neighboring sheets 32b and 32c have corresponding magnets 50b and 50c that have magnetic attraction to support alignment. Where each sheet 32 in the stack 48 that forms grid 30 is similarly constructed and the order of sheets 32 does not matter, the same pattern of magnet placement can be used on each of the neighboring sheets 30. In fabricating grid 30, the individual sheets 32 that form the grid 30 can be sequentially fitted onto the stack 48 in a sequence, such as by first registering only the edge of each subsequent sheet 32 to the existing stack 48 of sheets 32 and then unrolling the surface of the new sheet 32 onto the existing stack 48 to increasingly engage magnets in succession on each added sheet 32 and to reinforce magnetic attraction along the sheet 32 as it is rolled into position.

Figure 10B:
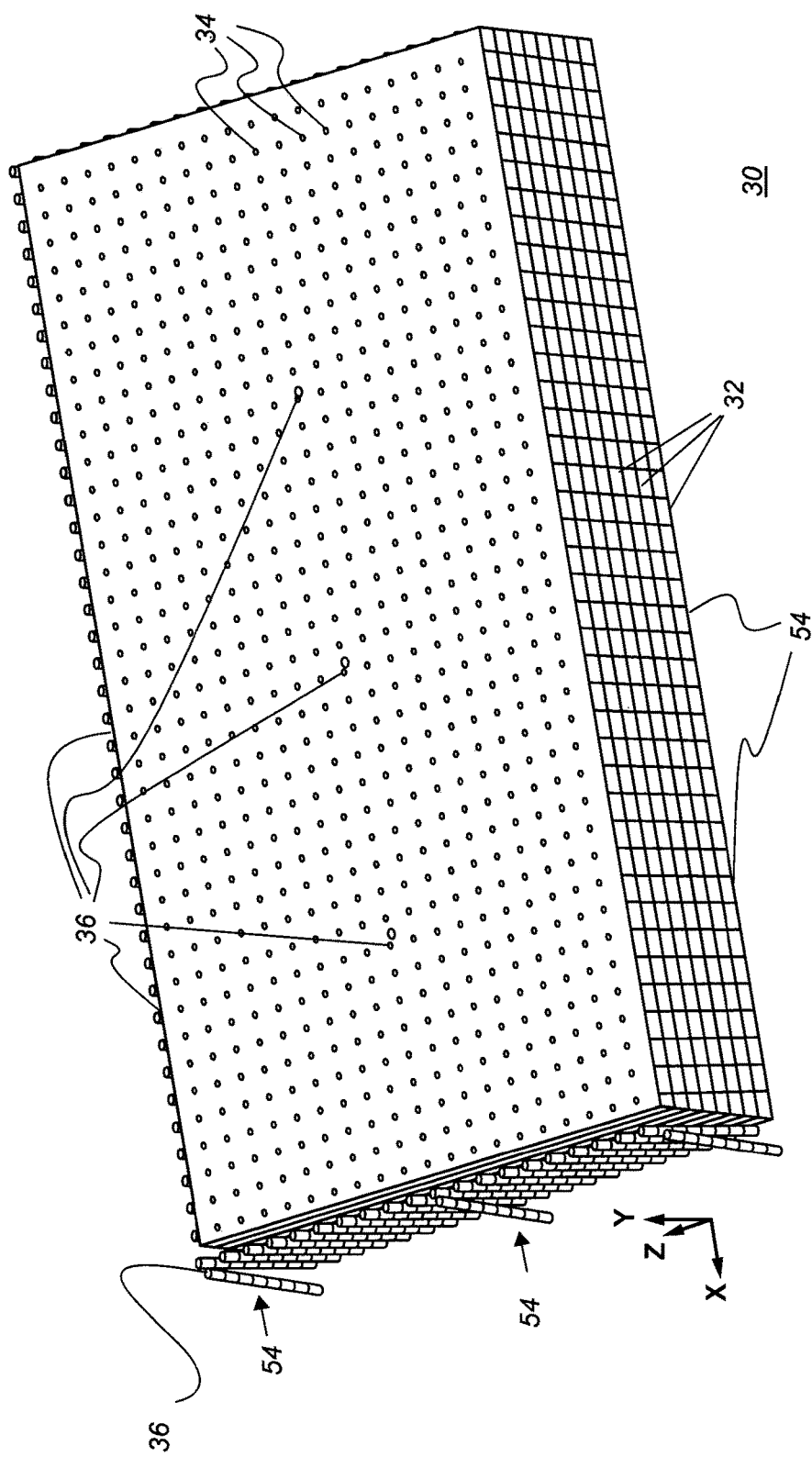
FIG. 10B is a perspective view that shows an exemplary stacking of sheets to form a grid, along with a number of columns of magnetized material.
Figure 10C:
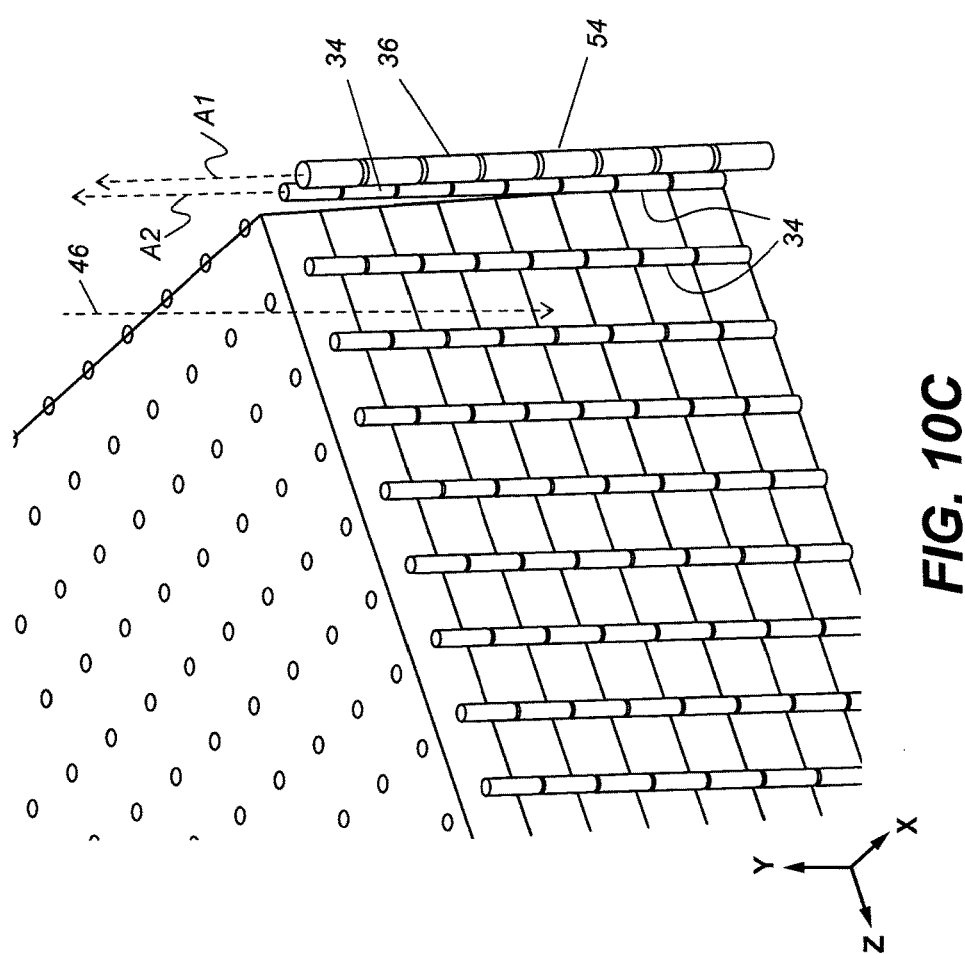
FIG. 10C is an enlarged perspective view that shows exemplary channels that extend between sheets.

FIG. 10B shows an arrangement of grid 30 formed from a stacking of sheets 32, not drawn to scale. Magnetized materials 38 are provided in cavities 36 that align in columns 54. As is particularly shown in the enlarged view of FIG. 10C, columns 54 that provide magnetic coupling and alignment may be arranged along axes A1. Axes A1 may be at angles that are offset from the angle A2 of cavities 34 that collectively form channels 46. For example, angle A2 may be normal while angle A1 is oblique, or vice versa, for portions of a focused grid in which cavities 36 are angled at normal, or other than a normal, to the sheet 32 surface. Columns 54 are shown as cylindrical and are shown distributed at spaced intervals along the stacked sheets 32.

FIG. 10B shows some details of grid 30 according to an embodiment of the present disclosure. In the exemplary embodiment shown, the section of grid 30 shown has approximate dimensions of about 10.0×5.0 mm There are eight layered sheets 32 shown, each sheet having approximately 0.20 mm thickness; there can be some incremental spacing between sheets due to cavity features, giving a total grid stack height of about 1.79 mm Protective film thickness of sealant layer 44 (FIG. 7D) is about 0.012 mm Cavity 34 diameter is approximately 0.05 mm Cavity 34 centerline is about 0.25 mm, nominal, so that 40 cavities/cm are provided in this example. Magnet column 54 diameter is approximately 0.10 mm.

One or more electromagnets can alternately be used to supplement the positional registration and coupling provided by permanent magnet materials of magnets 50a, 50b, 50c (FIG. 10A) between two or more sheets 32.

Magnet-assisted coupling and alignment between neighboring sheets 32 is advantageous because it allows some amount of flexure to the stack, so that rigidity is not a requirement for maintaining sheet 32 alignment. Instead, grid 30 can be flexibly bent or curved in order to adapt more closely to the path of incident radiation through a material object or a human or animal subject and to a receiver. As the stack 48 is bent, magnetic attraction still holds the sheets 32 together and supports restoring the grid 30 to a flat, planar state. The magnetic coupling between sheets 32 allows some measure of flexibility and movement between sheets, so that a roller of a given radius can be used to move the grid into and out from the image path. The flexible grid 30 can thus be transported about the radius of the roller, yet remain in the bucky 52, for example, as shown subsequently. Tensioned wires can be used to help separate sheets when bending or otherwise in flexure, such as about a roller.

One exemplary application in which flexure can be particularly useful is for x-ray imaging of large pipes, such as utility or chemical processing piping. The capability to wrap around the curved surface of the pipe or other structure has a number of advantages for non-destructive testing, for example.

Magnets can be formed by filling a subset of the cavities 36 with a liquid magnetizable material, then applying a blade or squeegee to the surface of the sheet, and then magnetizing the material after it sets. Sheets 32 can be polarized so that all cavities 36 are N-polarized on one side of the sheet and S-polarized on the opposite side. Alternately, magnetization itself can be patterned, so that, from the same side of the sheet 32, a portion of the filled cavities 36 are N-polarized and the remaining portion of the filled cavities 36 are S-polarized.

Other methods can alternately be used for coupling sheets 32 to each other in the stack. These include use of adhesives, fasteners, frames and other holders, and other devices. Magnetic coupling using micro-magnet structures such as cavities 36 is particularly advantaged, due to its capability for effecting precision alignment between sheets, at multiple points along the sheet surface.

Figure 11:
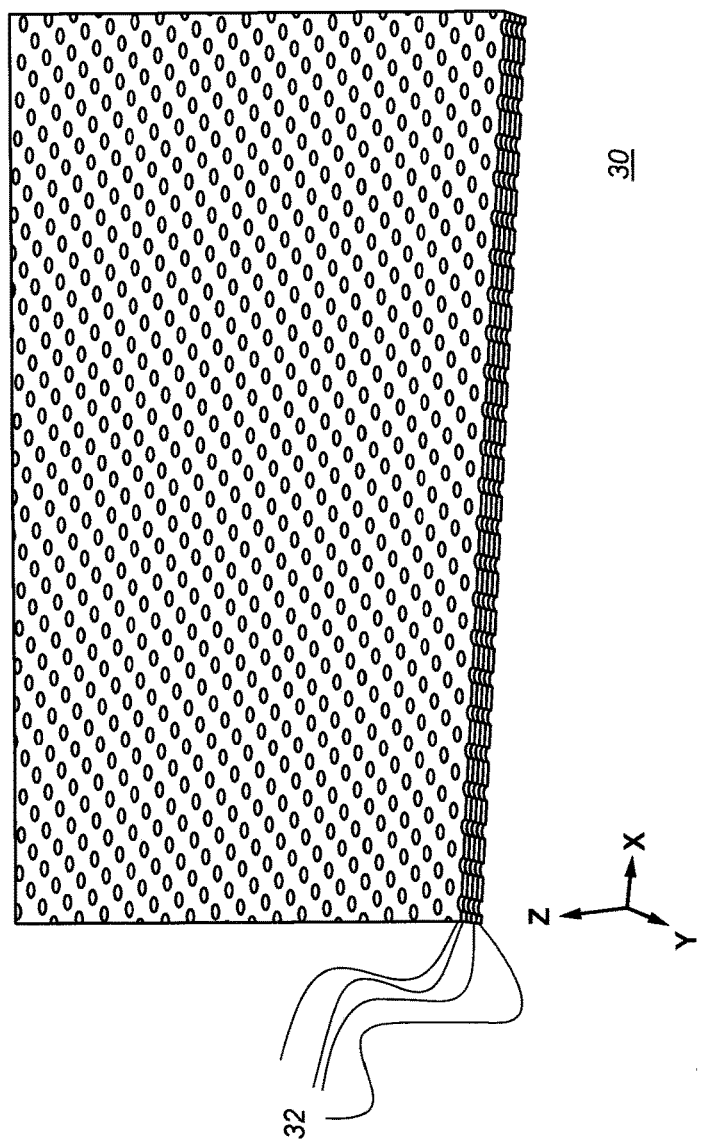
FIG. 11 shows a perspective view of a portion of an exemplary flexible grid formed according to an embodiment of the present disclosure.

The perspective view of FIG. 11 shows a portion of flexible grid 30 that is formed from individual sheets 32 according to an embodiment of the present disclosure. Numerous sheets 32 can be used, depending on the desired thickness and other characteristics. It can be appreciated that the use of individual sheets 32 allows grid 30 to have any of a number of desirable arrangements, for focused or unfocused grids.

Figure 12:
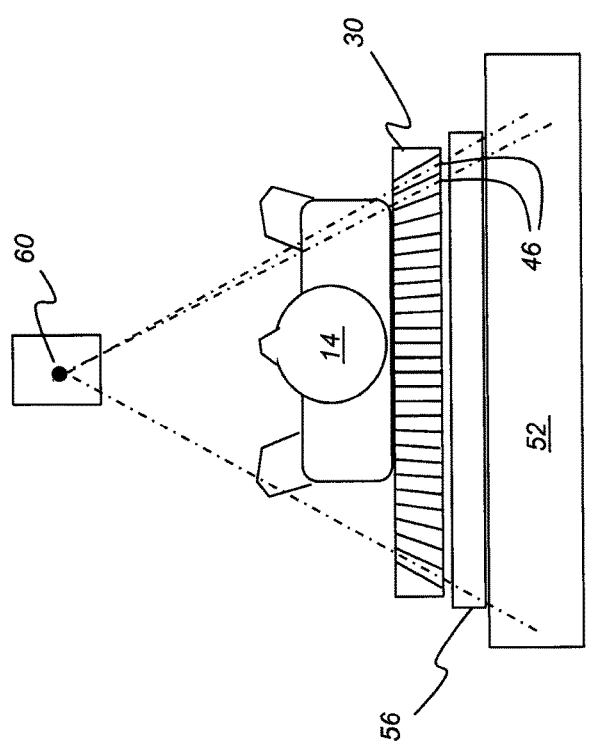
FIG. 12 is a schematic view showing components of an exemplary x-ray apparatus that uses the grid of the present disclosure.

The schematic view of FIG. 12 shows a focused grid 30, wherein channels 46 that extend through the grid 30, from sheet to sheet as described previously, substantially converge toward a focal point, shown as x-ray source 60. The position of a patient 14 and an x-ray detector 56 are also shown in FIG. 12. The x-ray detector 56 that is used for obtaining an image can be a digital radiography (DR) receiver or can be a film or computed radiography (CR) receiver, for example.

Figure 13:
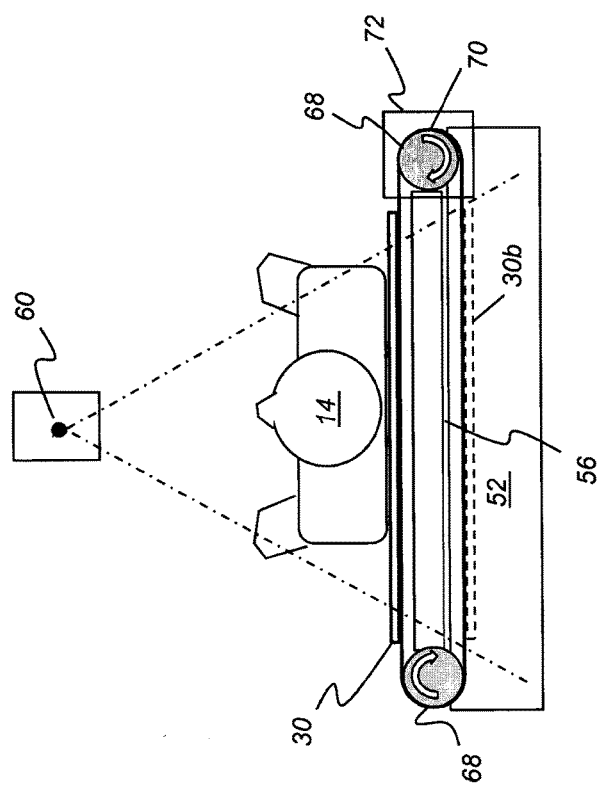
FIG. 13 is a schematic view showing exemplary components of an x-ray apparatus that has a grid mounted on a transport apparatus with rollers.

The schematic view of FIG. 13 shows an optional bucky 52 that has a transport apparatus 70 with rollers 68 or other mechanics that can be energized to move grid 30 from a first position in front of x-ray detector 56 to a second position, behind the x-ray detector 56. Because grid 30 can be formed from separable polymer sheets that can be magnetically coupled and aligned, grid 30 is flexible and can be transported around the radius of a roller or other curved surface. Grid channels 46 (FIG. 12) can be slightly out of alignment during transport, since registration of magnetic cavities 36 to each other can be restored automatically by the magnetic alignment feature. An actuator 72 rotates one or both rollers 68 in order to transport grid 30 between positions. Bucky 52 can also be energizable to use rotation in order to change grids. In such an embodiment, bucky 52 moves a second grid 30b (shown in dashed outline) having a different focal distance or arrangement of channels 46 in front of the x-ray detector 56 after the first grid 30 is moved out of position. Alternately, other types of transport apparatus can be used, providing U-shaped movement about a roller radius, for example.

Figure 14:
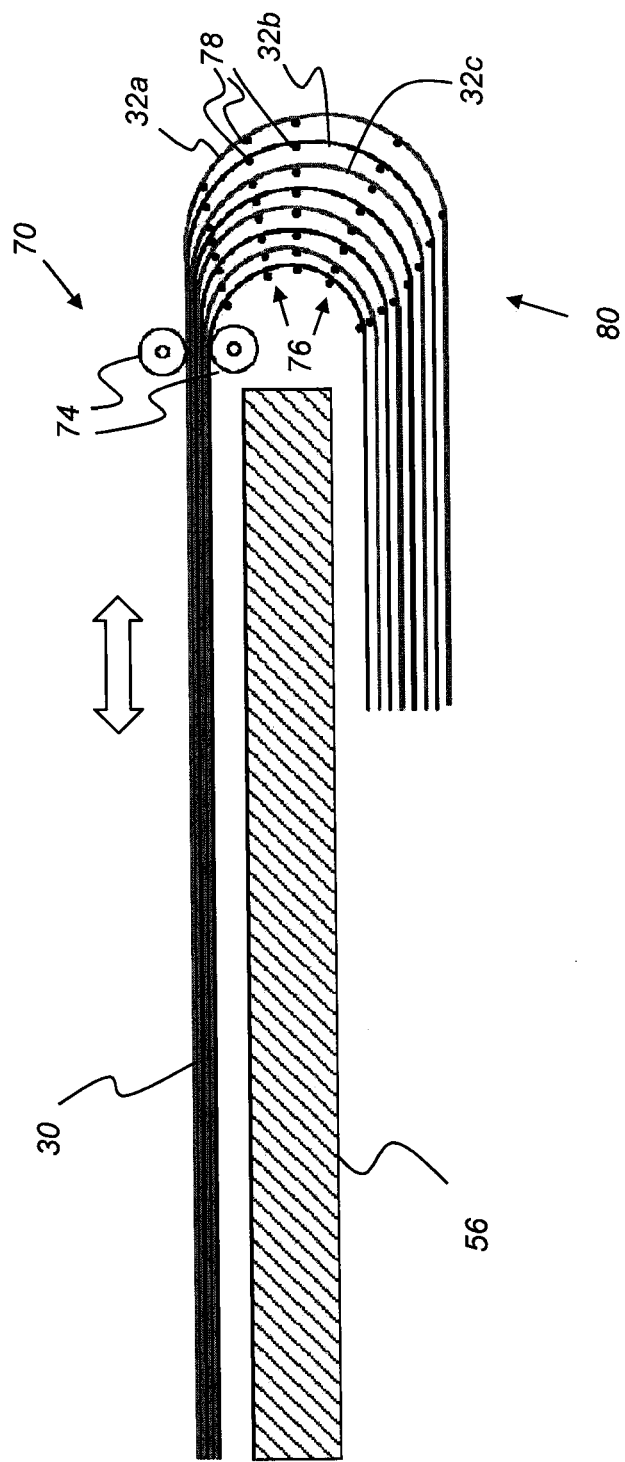
FIG. 14 is a schematic diagram showing an exemplary separation mechanism used to temporarily separate sheets in order to relieve grid stiffness for transport about a radius.

The top view schematic view of FIG. 14 shows a grid 30 in transport apparatus 70 wherein a separation mechanism 80 is used to temporarily separate sheets 32a, 32b, 32c, etc. in order to relieve grid 30 stiffness and allow grid 30 to be transported about a radius around an x-ray detector 56. According to the embodiment shown in FIG. 14, the separation mechanism 80 includes one or more combs 76 of wires 78 that extend through grid 30 orthogonal to the radius of curvature, shown as dots in the cross-section top view of FIG. 14. When grid 30 is moved past rollers 74 (to the right in the FIG. 14 view), combs 76 are manipulated by an optional actuator (not shown) or by spring tension that spreads the comb wires 78 outwards. This relaxes grid 30 thickness by causing sheets 32a, 32b, 32c, etc. to separate slightly from each other as grid 30 is driven around the turn radius. Wires 78 lie outside the corresponding image area of grid 30 and can be formed of stiff wire, such as piano wire or other stiff structure. According to an alternate embodiment of the present disclosure, combs 76 are held in place while grid 30 moves through the turn radius. Because the sheets 32a, 32b, 32c, etc. are magnetically attracted to each other, reversing the turn direction allows the grid 30 to reconstruct itself, with its cavities properly aligned for imaging when the grid 30 is transported back into imaging position.

The pattern of radio-opaque cavities 34 can be adapted to suit particular imaging requirements, with variable cavity angle and width and depth dimensions. Cavity shape and size can be different within the same sheet or in adjacent sheets 32 in the stack that forms grid 30. The channels 46 that extend through the stacked sheets 32 can substantially converge toward a focal point, such as toward the location of the x-ray source, as shown in FIG. 12. Grids having different focal lengths can be formed by placing inter-sheet spacers of different thicknesses between each sheet 32 in a grid. An inter-sheet spacer can be an untreated sheet of the same substrate that is used for forming sheet 32, for example.

The flexibility of grid 30 is a function of factors such as the substrate 40 that is selected for sheet 32 material, density and size of radio-opaque cavities 34, radio-opaque material 42 (FIG. 7C) used to fill radio-opaque cavities 34, sheet thickness, number of sheets 32 stacked together (FIG. 10B), and how the sheets 32 are coupled to each other.

While the invention has been described with reference to exemplary embodiments for flexible grid fabrication and use, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An antiscatter grid for radiological imaging, the antiscatter grid comprising:
 a stack of two or more flexible sheets, wherein each flexible sheet comprises:
  (i) a plurality of spaced apart opaque cavities, each opaque cavity containing a radio-opaque material, wherein the plurality of spaced apart opaque cavities define a plurality of channels extending through the stack of two or more flexible sheets that are transmissive to ionizing radiation; and
  (ii) a plurality of magnets that are disposed in or on each of the stack of two or more flexible sheets to couple each flexible sheet to one or more neighboring flexible sheets of the stack.

2. The antiscatter grid of claim 1, wherein the plurality of channels converge toward a focal point.

3. The antiscatter grid of claim 1, wherein the plurality of magnets are disposed in the plurality of spaced apart opaque cavities in the stack of two or more flexible sheets.

4. The antiscatter grid of claim 3, wherein the plurality of magnets comprise a liquid magnetizable material.

5. The antiscatter grid of claim 1, wherein the plurality of magnets include one or more electromagnets.

6. The antiscatter grid of claim 1, wherein the stack of two or more flexible sheets is configured to be placed into a moveable bucky.

7. The antiscatter grid of claim 1, wherein the radio-opaque material comprises is selected from the group consisting of tungsten and lead.

8. The antiscatter grid of claim 1, wherein a major surface of the stack of two or more flexible sheets comprises a protective coating thereon.

9. The antiscatter grid of claim 1, wherein the plurality of spaced apart opaque cavities are formed using a laser.

10. The antiscatter grid of claim 1, further comprising inter-sheet spacers between flexible sheets in the stack of two or more flexible sheets.

11. The antiscatter grid of claim 1, wherein the plurality of spaced apart opaque cavities are formed by simultaneously forming holes through the stack of two or more flexible sheets.

12. The antiscatter grid of claim 1, wherein the plurality of spaced apart opaque cavities are formed while bending the stack of two or more flexible sheets.

13. The antiscatter grid of claim 1, wherein the plurality of spaced apart opaque cavities comprise a substantially uniform size and spacing.

14. The antiscatter grid of claim 1, wherein the plurality of spaced apart opaque cavities comprise varied size or spacing along the stack of two or more flexible sheets.

15. The antiscatter grid of claim 1, wherein the stack of two or more flexible sheets comprise sufficient flexibility to be wrapped about a curved surface.

16. A radiological imaging system comprising:
 an x-ray source;
 an x-ray detector; and
 a first antiscatter grid, the first antiscatter grid comprising
  a stack of two or more flexible sheets, each flexible sheet comprising:
   a plurality of spaced-apart opaque cavities, wherein each opaque cavity contains a radio-opaque material, and wherein the plurality of spaced apart opaque cavities define a plurality of radio-lucent channels extending through the first antiscatter grid; and
   a plurality of magnets disposed along the flexible sheet to couple the flexible sheet to one or more neighboring flexible sheets of the stack.

17. The radiological imaging system of claim 16, further comprising a transport assembly, the transport assembly energizable to move the first antiscatter grid to a position in front of at least a portion of the x-ray detector and to a position behind at least a portion of the x-ray detector.

18. The radiological imaging system of claim 17, further comprising one or more combs of wires to separate the stack of two or more flexible sheets as the transport assembly moves the first antiscatter grid.

19. The radiological imaging system of claim 18, wherein the one or more combs of wires extend along one or more side edges of the first antiscatter grid.

20. The radiological imaging system of claim 17, further comprising a second antiscatter grid, wherein the transport assembly is further energizable to move at least a portion of the second antiscatter grid to the position in front of the x-ray detector.

* * * * *